United States Patent [19]
Thomas et al.

[11] Patent Number: 5,334,718
[45] Date of Patent: Aug. 2, 1994

[54] CHEMICAL PROCESS AND INTERMEDIATES USED THEREIN

[75] Inventors: Andrew P. Thomas, Congleton; David M. G. Martin, Stockport; Stanley A. Lee; Lyn Powell, both of Macclesfield, all of England

[73] Assignee: Zeneca Limited, London, England

[21] Appl. No.: 7,930

[22] Filed: Jan. 25, 1993

[30] Foreign Application Priority Data

Jan. 28, 1992 [GB] United Kingdom ............. 9201715.1

[51] Int. Cl.$^5$ ............................................ C07D 471/04
[52] U.S. Cl. ...................................... 546/118; 544/328; 544/331
[58] Field of Search ................. 546/118; 544/328, 331

[56] References Cited

FOREIGN PATENT DOCUMENTS

| 2024137 | 3/1991 | Canada . |
|---------|--------|----------|
| 399731 | 11/1990 | European Pat. Off. . |
| 400974 | 12/1990 | European Pat. Off. . |
| 420237 | 4/1991 | European Pat. Off. . |
| 426021 | 5/1991 | European Pat. Off. . |
| 434038 | 6/1991 | European Pat. Off. . |
| 495626 | 7/1992 | European Pat. Off. . |

OTHER PUBLICATIONS

G. Bianchetti, et al., "Distacco per Idrazinolisi del Gruppo 2,4-Dinitrofenilico.-Nota II. Idrazinolisi di 1-(2,4-dinitro)-fenil-v-triazoli e-tetrazoli" *Gazz. Chim. Ital.*, 1964, 94, 340-350.

*Primary Examiner*—Bernard Dentz
*Attorney, Agent, or Firm*—Cushman, Darby & Cushman

[57] ABSTRACT

The invention provides a novel chemical process for the manufacture of certain imidazo[4,5-b]pyridine derivatives of the formula I wherein $R^1$, $R^2$, $R^3$ and $R^4$ have the various meanings defined herein, and their non-toxic salts, which are angiotensin II inhibitors. The process involves the removal of an electron-deficient phenyl group or a pyridyl or pyrimidyl group from a compound of the formula II as defined herein. Certain of the intermediates are novel and are provided as a further feature of the invention.

11 Claims, No Drawings

CHEMICAL PROCESS AND INTERMEDIATES USED THEREIN

This invention concerns a novel chemical process for the production of certain imidazo[4,5-b]pyridine derivatives, which derivatives possess pharmacologically useful properties in antagonising at least in part one or more of the actions of substances known as angiotensins, and in particular of that known as angiotensin II (hereinafter referred to as "AII"). The invention also concerns various derivatives which are valuable chemical intermediates, for example for use in the abovementioned process.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced from the blood plasma protein angiotensinogen by the action of the enzyme renin. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Compounds which antagonise one or more of the actions of AII are useful for the reduction or prevention of these effects produced by the action of AII. There remains a continuing need for alternative AII antagonists and for effective synthetic procedures for their production such as that provided by this invention.

In our European Patent Application, Publication No. 399,731 there is described a series of imidazo[4,5-b]pyridines which possess AII antagonist properties and which includes compounds of the formula I (set out hereinafter, together with the other chemical formulae identified by Roman numerals) wherein $R^1$ is (1–6C)alkyl; is $R^2$ is hydrogen or halogeno; and $R^3$ and $R^4$ are selected from hydrogen, halogeno, (1–6C)alkyl, (1–6C)alkoxy, hydroxymethyl and hydroxy; and physiologically acceptable salts thereof. Particular values for $R^1$ (or for $R^3$ or $R^4$ when either is alkyl) include, for example, methyl, ethyl, propyl and butyl. Particular values for $R^2$ include, for example, hydrogen, fluoro, chloro and bromo, or which hydrogen is generally preferred. Particular values for $R^3$ or $R^4$ when it is alkoxy include, for example, methoxy and ethoxy, and when it is halogeno include, for example, fluoro, chloro and bromo. Preferred compounds disclosed in said European application include:

2-butyl-3-[(2'-(1H-tetrazol-5-yl)biphenyl-4-yl)methyl]-3H-imidazo[4,5-b]pyridine;
2-butyl-7-methyl-3-[(2'-(1H-tetrazol-5-yl)biphenyl-4-yl)methyl]-3H-imidazo[4,5-b]pyridine;
2-butyl-5-methyl-3-[(2'-(1H-tetrazol-5-yl)biphenyl-4-yl)methyl]-3H-imidazo[4,5-b]pyridine;
2-butyl-7-chloro-3-[(2'-(1H-tetrazol-5-yl)biphenyl-4-ylmethyl]-3H-imidazo[4,5-b]pyridine; and
2-butyl-6-(hydroxymethyl)-3-[(2'-(1H-tetrazol-5-yl)biphenyl-4-yl)methyl]imidazo[4,5-b]pyridine;
and the physiologically acceptable salts thereof.

In addition, European Patent Application, Publication No. 400974 discloses other imidazo[4,5-b]pyridines which are AII antagonists. Certain of these compounds are within the group of compounds of formula I defined above. One such compound which is of particular interest as an AII antagonist is the compound: 2-ethyl-5,7-dimethyl-3-[(2'-(1H-tetrazol-5-yl)biphenyl-4-yl)methyl]-3H-imidazo-[4,5-b]pyridine; or a physiologically acceptable salt thereof.

We have now discovered a particularly effective process for the manufacture of the above mentioned imidazo[4,5-b]pyridine AII antagonists and this is the basis of our invention.

According to the invention there is provided a process for the manufacture of an imidazo[4,5-b]pyridine of the formula I defined above, or a physiologically acceptable salt thereof, which comprises reaction of a compound of the formula II wherein $P^1$ is an electron-deficient phenyl group or is a pyridyl or pyrimidyl group, and $R^1$, $R^2$, $R^3$ and $R^4$ have any of the meanings defined above, with a base selected from an alkali metal hydroxide, (1–12C)alkanolate, (1–12C)alkanethiolate, phenolate, thiophenolate and diphenylphosphide, wherein any phenyl ring of the latter three groups may optionally bear a (1–4C)alkyl, (1–4C)alkoxy or halogeno substituent.

A particular value for $P^1$ when it is an electron-deficient phenyl group includes, for example, a phenyl group bearing 1, 2 or 3 electron-withdrawing groups independently selected from halogeno (typically chloro or bromo), nitro, cyano, trifluoromethyl, di(1–4C)alkylaminosulphonyl (such as dimethylaminosulphonyl or diethylaminosulphonyl) and (1–4C)alkylsulphonyl (such as methylsulphonyl or ethylsulphonyl).

Suitable bases include, by way of example:
for an alkali metal hydroxide: sodium or potassium hydroxide;
for an alkali metal alkanolate: an alkali metal (1–8C)alkanolate, for example an alkali metal (1–4C)alkoxide, such as sodium or potassium methoxide, ethoxide, propoxide or butoxide;
for an alkali metal alkanethiolate: an alkali metal (1–8C)alkanethiolate, for example an alkali metal (1–4C)alkanethiolate such as sodium or potassium methanethiolate, ethanethiolate, propanethiolate or butanethiolate;
for a phenolate or thiophenolate: the sodium or potassium salt of phenol, thiophenol, or a phenol or thiophenol bearing a methyl, ethyl, methoxy, ethoxy, fluoro, chloro, bromo or iodo group.

A particular value for an optional substituent on a phenyl group of an alkali metal phenolate, thiophenolate or diphenylphosphide, when it is alkyl is, for example, methyl or ethyl; when it is alkoxy is, for example, methoxy or ethoxy; and when it is halogeno is, for example, fluoro, chloro or bromo.

A preferred value for $P^1$ is, for example, a nitrophenyl group or a 4-pyridyl, 4-cyanophenyl, 4-dimethylaminosulphonyl, 4-methylsulphonyl or 3-cyano-4-trifluoromethylphenyl group. Of these values, 4-nitrophenyl is especially preferred.

A particularly preferred base is an alkali metal alkanethiolate such as sodium or potassium propanethiolate, an alkali metal alkanolate such as sodium or potassium methoxide or ethoxide, or an alkali metal thiophenolate such as sodium or potassium 4-fluorothiophenolate.

It will be appreciated that when the base is an alkali metal alkanolate, alkanethiolate, phenolate, thiophenolate or diphenylphosphide, it may conveniently be generated in situ from the corresponding alkanol, alkanethiol, phenol, thiophenol or diphenylphosphine with a suitable alkali metal base such as an alkali metal hydride, for example, lithium, potassium or sodium hydride. Alternatively, when an alkali metal alkanolate is used, it may be convenient to employ the base as a solution in the corresponding alcohol (for example a solution of sodium methoxide in methanol). When an alkanethiolate is used as the base, this may also be generated in situ from the corresponding alkanethiol with an alkali metal alkanolate (for example sodium methoxide, which itself may be in the form of a solution of sodium methoxide in methanol). The amount of base used in the process is generally 1 equivalent or more, for example from 1 to 12 equivalents may be used, preferably from 1 to 2.5 equivalents.

The process is generally carried out in a suitable inert organic solvent or diluent, for example, a polar solvent such as N,N-dimethylformamide or N-methylpyrrolidone. Alternatively, an alkanol such as methanol or ethanol may be used, for example, when an alkali metal hydroxide or alkoxide such as sodium or potassium hydroxide, methoxide or ethoxide is employed as base.

The process is generally carried out at a temperature in the range, for example, $-30°$ C. to $80°$ C. It will be appreciated that the choice of temperature selected depends on the nature of the base employed. For example, when an alkali metal alkanethiolate or alkanolate is used, a temperature in the range of $0°$ C. to $30°$ C. (conveniently at or about ambient temperature) is preferred. Similarly, when an alkali metal alkoxide is employed as base, the process may conveniently be performed at or near the boiling point of the corresponding alkanol, for example at about $40°$ to $80°$ C.

The starting materials of the formula II as defined hereinbefore may be obtained, for example, by alkylation of an imidazo[4,5-b]pyridine of the formula III wherein $R^1$, $R^3$ and $R^4$ have any of the meanings defined above, with a compound of the formula IV wherein $P^1$ and $R^2$ have any of the meanings defined hereinbefore and Hal. stands for a halogeno group such as chloro, bromo or iodo.

The alkylation may be carried using conditions already well known in the art for analogous alkylations. Thus, it may be performed in the presence of a suitable base, for example, an alkali metal alkoxide such as sodium methoxide or sodium ethoxide, an alkali metal carbonate such as sodium carbonate or potassium carbonate, or an alkali metal hydride such as sodium hydride or an organic base such as diisopropylethylamine and in a solvent or diluent, for example, a (1–4C)alkanol such as methanol or ethanol when an alkali metal alkoxide is used, or in a polar solvent such as N,N-dimethylformamide or N-methylpyrrolidone and at a temperature in the range, for example, $10°-100°$ C. Alternatively, a quaternary ammonium hydroxide may be used in a mixture of an aqueous or non-aqueous solvent such as water and dichloromethane. In some cases, the alkylation may produce a mixture containing the desired compound of formula II together with one or two isomers thereof, requiring purification of the intially formed alkylation mixture by a conventional procedure, for example by fractional crystallisation or chromatography.

The starting imidazo[4,5-b]pyridines may themselves be obtained by known procedures, for example, as described in the aforementioned European Patent Applications. Similarly, the compounds of formula IV may be obtained from the appropriate 2-bromobenzoic acid and amine of the formula $P^1.NH_2$, for example, as shown in Scheme 1 hereinafter (for Hal.=bromo).

Whereafter, when a physiologically acceptable salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, for example when one or more of $R^1$, $R^2$ and $R^3$ is an asymmetrically substituted alkyl, the aforesaid process may be carried out using the appropriate optically active form of the starting material of formula II. Alternatively, a racemic form of a compound of formula I may be resolved using a conventional procedure.

It will be appreciated that an alternative process variant of the present invention involves the use of a starting material of formula I in which the group $P^1$ is attached to the 2-nitrogen atom of the tetrazole ring rather than to the 1-nitrogen atom as specified hereinabove. The necessary starting materials for such a process variant may be made by methods well known in the art for the preparation of structurally analogous compounds.

The process of the invention is particularly advantageous for the production of the compounds of formula I (and especially of compounds such as: 2-butyl-3-[(2'-(1H-tetrazol-5-yl)biphenyl-4-yl)methyl]-3H-imidazo-[4,5-b]pyridine; or 2-ethyl-5,7-dimethyl-3[(2'-(1H-tetrazol-5-yl)biphenyl-4-yl)methyl]-3H-imidazo[4,5-b]pyridine or of physiologically acceptable salts thereof, with high purity, such as is required for their intended pharmaceutical use.

The intermediates of formula II as defined hereinabove are novel and are provided as a further feature of the invention.

The invention will now be illustrated by the following non-limiting Example in which, unless otherwise stated:

(i) concentrations and evaporations were carried out by rotary evaporation in vacuo;

(ii) operations were carried out at room temperature, that is in the range $18°-26°$ C.;

(iii) yields, where given, are intended for the assistance of the reader only and are not necessarily the maximum attainable by diligent process development;

(iv) $^1$H NMR spectra were normally determined at 270 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multplet; t, triplet; br, broad; d, doublet; and (v) the term "1H-tetrazol-5-yl" is the abbreviated version of "1H-1,2,3,4-tetrazol-5-yl".

EXAMPLE 1

A solution of sodium methoxide in methanol (30% w/v, 4 mL) was added to a solution of 2-ethyl-5,7-dimethyl-3-[(2'-(1-(4-nitrophenyl)-1H-tetrazol-5-yl)biphenyl-4-yl)methyl]-3H-imidazo[4,5-b]pyridine (A) (1.0 g) in methanol (20 mL) and the mixture was heated under reflux for 18 hours. The mixture was cooled to ambient temperature and solvent was removed by evaporation. The residue was dissolved in water (50 mL) and the solution was extracted with ether (2×50 mL). The aqueous layer was separated and adjusted to pH 5 with 1M citric acid solution. The product was collected by filtration and dried to give 2-ethyl-5,7-dimethyl-3-[(2'-(1H-tetrazol-5-yl)biphenyl-4-yl)methyl]-3H-imidazo[4,5-b]pyridine (0.6 g) as a solid, m.p. 175°-177° C. (decomposition); NMR ($d_6$-acetone): 1.26(t, 3H), 2.50(s, 3H), 2.53(s, 3H), 2.76(q, 2H), 5.49(s, 2H), 6.91(s, 1H), 7.07(d, 2H), 7.14(d, 2H), 7.6(m, 3H), 7.75(dd, 1H); mass spectrum (+ve fast atom bombardment (FAB), DMSO nitrobenzyl alcohol): 410(M+H)+; microanalysis, found C, 64.9; H, 5.6; N, 22.0%; $C_{24}H_{23}N_7.2.0H_2O$ requires: C, 64.7; H, 6.0; N, 22.0%.

The starting material A was prepared as follows:

(i) Thionyl chloride (120.5 g) was added to a stirred mixture of 2-bromobenzoic acid (194.0 g) in toluene (500 mL) and N,N-dimethylformamide (DMF) (5 mL) and the mixture heated at 80° C. for 4 hours. The solution was cooled to 20° C. and added slowly to a solution of 4-nitroaniline (133.1 g) in toluene (500 mL) and N-methylpyrrolidone (NMP) (120 mL), maintaining the temperature of the reaction mixture between 20°-25° C. The reaction mixture was then stirred for 24 hours, during which time a solid precipitated. Water (360 mL) was added with rigorous stirring. The suspended solid was collected by filtration, and washed successively with water, toluene and acetonitrile to give 2-bromo-N-(4-nitrophenyl)benzamide (B) as a solid, in 87% yield; m.p. 200°-202° C.; NMR ($d_6$-DMSO): 7.4-7.8(m, 7H), 8.0(d, 2H), 8.3(d, 2H), 11.5(br s, 1H). This material was used without further purification in step (ii).

(ii) Triethylamine (1.04 g; 10.38 mM) was added to a mixture of amide B (3.0 g; 9.35 mM) in acetonitrile (12 mL) and DMF (0.189 g; 2.58 mM) and the mixture was stirred for 90 minutes. Thionyl chloride (1.44 g; 12.14 mM) was then added slowly, keeping the reaction temperature below 25° C. The mixture was stirred for 5 hours at ambient temperature and then cooled to 10° C. Triethylamine (2.83 g; 8 mM) was then added, followed by sodium azide (1.33 g; 20.4 mM) and tetrabutylammonium bromide (0.42 g; 1.3 mM). The mixture was stirred for 2 hours at 10° C. and then allowed to warm to ambient temperature and stirring continued for 24 hours. The mixture was poured into excess water and the precipitated solid collected by filtration. The solid was purified by trituration with a hot mixture of ethyl acetate (26 mL), hexane (2.6 mL) and triethylamine (0.1 mL) to give 5-(2-bromophenyl)-1-(4-nitrophenyl)-1H-tetrazole (C) (2.36 g; 73% yield) as an off-white solid, m p. 169°-170° C.;

NMR ($d_6$-acetone; 270 MHz): 7.61-7.86(m, 6H), 8.41(d, 2H); microanalysis, found: 44.8; H, 2.3; N, 20.2; Br, 23.1%.

(iii) A mixture of 4-methylphenyl boronic acid (9.7 g; 71 mM), sodium carbonate (16.7 g; 158 mM), water (100 mL), methanol (50 mL) and toluene (50 mL) was heated to 60° C. to give a clear solution. Compound C (20.0 g; 55 mM) was then added, followed by tetrakis(triphenylphosphine)palladium (0.3 g; 0.25 mM) and the mixture was heated under reflux for 3 hours. Toluene (30 mL) was added and the warm mixture was filtered through diatomaceous earth. The organic phase was separated and the aqueous phase was extracted with toluene (40 mL). The combined organic phases were evaporated to give a solid which was recrystallised from toluene/petroleum ether (100°-120° C.) (1:1 v/v) to give 5-(4'-methylbiphenyl-2-yl)-1-(4-nitrophenyl)-1H-tetrazole (D)(18.7 g; 90% yield), m.p. 164°-166° C.; NMR ($CDCl_3$): 2.3(3H, s), 6.45(2H, d), 6.85(4H, m), 7.38(1H, d), 7.65(2H, m), 7.85(1H, d), 8.0(2H, d).

(iv) A mixture of compound D (8.0 g; 21 mM), N-bromosuccinimide (4.53 g; 25 mM) and azo(-bisisobutyronitrile) (73 mg) in 1,1,1-trichloroethane (methyl chloroform) (50 mL) was heated under reflux for 4 hours. The mixture was cooled to ambient temperature, washed with water (3×50 mL), and the suspended solid collected by filtration to give 5-(4'-bromomethylbiphenyl-2-yl)-1-(4-nitrophenyl)-1H-tetrazole (E) (7.3 g), m.p. 192°-195° C.; NMR ($CDCl_3$): 4.4(2H, s), 6.52(2H, d), 6.85(2H, d), 7.07(2H, d), 7.4(1H, d) 7.7 (2H,m), 7.9(1H, d).

(v) 2-Ethyl-5,7-dimethylimidazo[4,5-b]pyridine (obtained as described in European Patent Application, Publication no. 400974) (2.0 g) was added to a mixture of potassium carbonate (4 g) and compound E (6.0 g) in 1,2-dimethoxyethane (100 mL). The mixture was heated at 60° C. for 2.5 hours, then cooled to ambient temperature and saturated sodium chloride solution added. This mixture was extracted with ethyl acetate (2×100 mL) and the combined extracts dried ($MgSO_4$). Solvent was removed by evaporation and the residue was purified by flash chromatography eluting with ethyl acetate/hexane (1:1 v/v) to give 2-ethyl-5,7-dimethyl-3-[(2'-(1-(4-nitrophenyl)-1H-tetrazol-5-yl)biphenyl-4-yl)methyl]-3H-imidazo[4,5-b]pyridine (A) (3.1 g) as a gum; NMR ($CDCl_{13}$): 1.40(t, 3H), 2.64(s, 3H), 2.68(s, 3H), 2.86(q, 2H), 5.39(s, 1H), 6.47(d, 2H), 6.71(m, 4H), 6.79(d, 2H), 6.97(s, 1H), 7.35(m, 1H), 7.65(m, 2H), 7.75(m, 2H), 7.85(m, 1H); mass spectrum (+ve FAB, DMSO/nitrobenzyl alcohol): 531(M+H)+.

Scheme 1

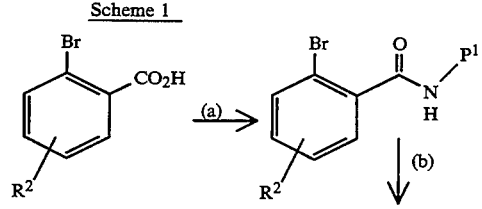

Scheme 1

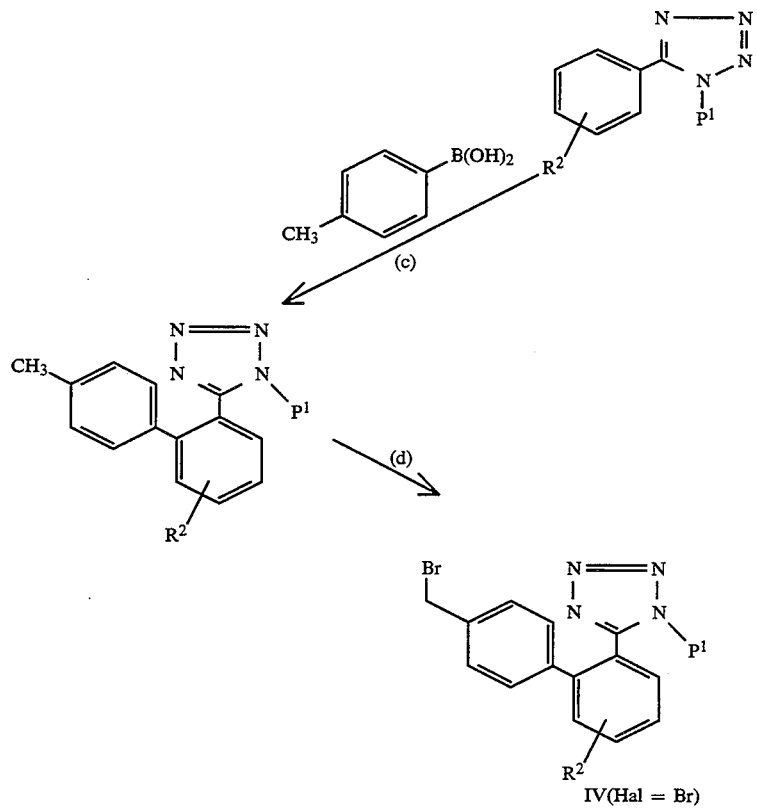

Reaction conditions:

(a) SOCl₂, DMF, toluene, 80° C.; then add to p¹.NH₂, toluene, N-methylpyrrolidone at ambient temperature
(b)
  (i) ET₃N, CH₃CN, DMF;
  (ii) SOCl₂, 10° C.; and
  (iii) Et₃N, NaN₃, tetrabutylammonium bromide, 10° C. to ambient temperature
(c) Add product of product from (b) and (Ph₃P)₄Pd to pre-formed solution of (4-CH₃)phenylboronic acid, Na₂CO₃, MeOH, and toluene, 60° C.; then heat under reflux
(d) N-bromosuccinimide, azo(bisisobutyronitrile), CH₃CCl₃

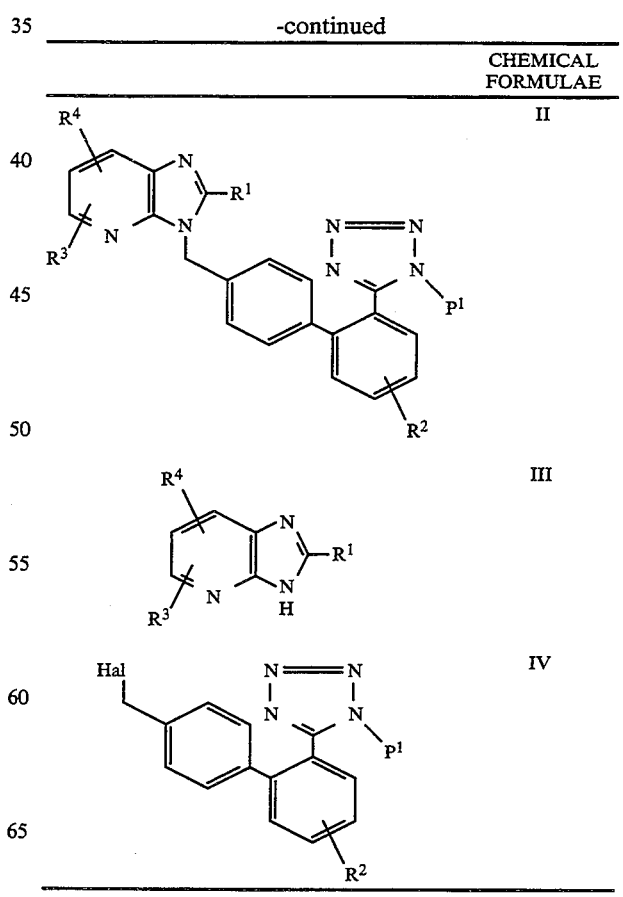

What we claim is:
1. A process for the manufacture of an imidazo [4,5-b]pyridine of the formula I

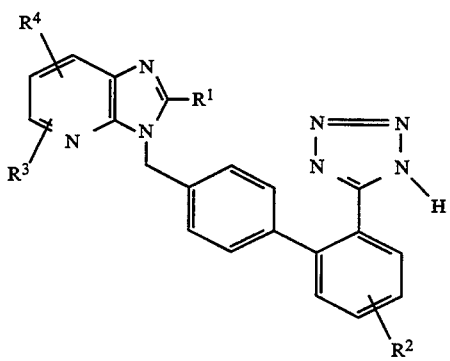

or a physiologically acceptable salt thereof, wherein $R^1$ is (1–6C)alkyl; $R^2$ is hydrogen or halogeno; and $R^3$ and $R^4$ are selected from hydrogen, halogeno, (1–6C)alkyl, (1–6C)alkoxy, hydroxymethyl and hydroxy; which is characterised in that a compound of the formula II

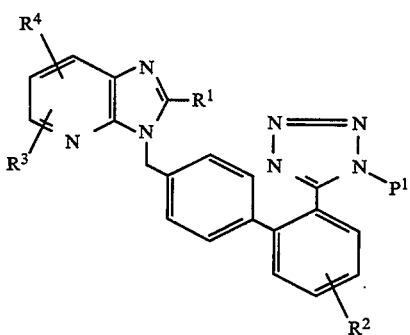

wherein $P^1$ is an electron-deficient phenyl group or is a pyridyl or pyrimidyl group, is reacted with a base selected from an alkali metal hydroxide, (1–12C)alkanolate, (1–12C)alkanethiolate, phenolate, thiophenolate and diphenylphosphide, wherein any phenyl ring of the latter three groups may optionally bear a (1–4C)alkyl, (1–4C)alkoxy or halogeno substituent; whereafter: when a physiologically acceptable salt of a compound of formula I is required, it is obtained by reaction with the appropriate acid or base affording a physiologically acceptable ion, or by any other conventional salt formation procedure; and when an optically active form of a compound of formula I is required, the process is carried out with an optically active form of the starting material of formula II, or a racemic form of a compound of formula I is resolved using a conventional procedure; and wherein $R^1$, $R^2$, $R^3$, $R^4$ and $P^1$ have any of the meanings defined above.

2. A process as claimed in claim 1 wherein, in the starting material of formula II, $P^1$ is a phenyl group bearing 1, 2 or 3 electron-withdrawing groups independently selected from halogeno, nitro, cyano, trifluoromethyl, di(1–4C)alkylaminosulphonyl or (1–4C) alkylsulphonyl.

3. A process as claimed in claim 1 wherein, in the starting material of formula II, $P^1$ is 4-nitrophenyl.

4. A process as claimed in claim 1 wherein the base is selected from sodium hydroxide, potassium hydroxide, sodium methoxide, potassium methoxide, sodium ethoxide, potassium propoxide, sodium butoxide, potassium butoxide, sodium methanethiolate, potassium methanethiolate, sodium ethanethiolate, potassium ethanethiolate, sodium propanethiolate, potassium propanethiolate, sodium butanethiolate, potassium butanethiolate, sodium phenolate and potassium phenolate, sodium thiophenolate and potassium thiophenolate, the phenyl ring of which last four bases being unsubstituted or bearing a methyl, ethyl, methoxy, ethoxy, fluoro, chloro, bromo or iodo group.

5. A process as claimed in claim 1 wherein the base is selected from an alkali metal alkanethiolate, an alkali metal alkanolate and an alkali metal thiophenolate.

6. A process as claimed in claim 1 wherein the base is an alkali metal alkanethiolate and is generated in situ from the corresponding alkanethiol with an alkali metal hydride or alkanolate.

7. A process as claimed in claim 5 or 6 wherein the reaction is carried out at a temperature in the range 0° to 30° C.

8. A process as claimed in claim 1 wherein from 1 to 2.5 equivalents of base are used.

9. A process as claimed in claim 1 wherein N-methylpyrrolidone is present as solvent or diluent.

10. A process as claimed in claim i for the preparation of an imidazo[4,5-b]pyridine of the formula I selected from 2-butyl-3-[(2'-(1H-tetrazol-5-yl)biphenyl-4-yl)-methyl]-3H-imidazo-[4,5-b]pyridine and 2-ethyl-5,7-dimethyl-3-[(2'-(1H-tetrazol-5-yl)biphenyl-4yl)methyl]-3H-imidazo[4,5-b]pyridine), or of a physiologically acceptable salt thereof.

11. A compound of the formula II

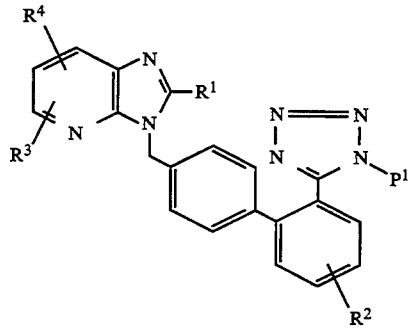

in either a racemic or optically active form; wherein $P^1$ is an electron-deficient phenyl group or is a pyridyl or pyrimidyl group; and wherein $R^1$ is (1–6C)alkyl; $R^2$ is hydrogen or halogeno; and $R^3$ and $R^4$ are selected from hydrogen, halogeno, (1–6C) alkyl, (1–6C) alkoxy, hydroxymethyl and hydroxy.

* * * * *